(12) United States Patent
Doerr

(10) Patent No.: US 8,818,521 B2
(45) Date of Patent: Aug. 26, 2014

(54) IMPLANTABLE MEDICAL DEVICE

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 912 days.

(21) Appl. No.: 12/474,093

(22) Filed: May 28, 2009

(65) Prior Publication Data
US 2009/0312821 A1    Dec. 17, 2009

(30) Foreign Application Priority Data

Jun. 11, 2008  (DE) .......................... 10 2008 002 369

(51) Int. Cl.
| | | |
|---|---|---|
| *A61N 1/08* | (2006.01) | |
| *A61N 1/372* | (2006.01) | |
| *G06F 19/00* | (2011.01) | |

(52) U.S. Cl.
CPC ........ *A61N 1/37276* (2013.01); *G06F 19/3406* (2013.01)
USPC .......................................................... 607/60

(58) Field of Classification Search
USPC .......................................................... 607/60
See application file for complete search history.

(56) References Cited

U.S. PATENT DOCUMENTS

| | | | |
|---|---|---|---|
| 6,472,991 B1 | 10/2002 | Schulman et al. | |
| 7,650,185 B2 * | 1/2010 | Maile et al. ...................... | 607/16 |
| 2003/0114898 A1 | 6/2003 | Von Arx et al. | |
| 2003/0119568 A1 * | 6/2003 | Menard ........................... | 455/572 |
| 2003/0149459 A1 | 8/2003 | Von Arx et al. | |
| 2005/0113886 A1 * | 5/2005 | Fischell et al. .................. | 607/60 |
| 2006/0025834 A1 | 2/2006 | Von Arx et al. | |
| 2008/0009921 A1 * | 1/2008 | Mosesov et al. ................ | 607/60 |
| 2008/0294219 A1 * | 11/2008 | Osypka et al. .................. | 607/32 |

FOREIGN PATENT DOCUMENTS

| | | |
|---|---|---|
| DE | 10111059 | 10/2001 |
| EP | 1 82 011 | 2/2008 |
| WO | WO 03/024322 | 3/2003 |
| WO | WO 2006/114297 | 11/2006 |

OTHER PUBLICATIONS

European Search Report, dated Jul. 27, 2009.
German Search Report, dated Apr. 27, 2009.

* cited by examiner

*Primary Examiner* — Carl H Layno
*Assistant Examiner* — Jennifer Ghand
(74) *Attorney, Agent, or Firm* — ARC IP Law, PC; Joseph J. Mayo

(57) ABSTRACT

Implantable medical device (10) having control unit (20) connected to bidirectional wireless interface (18) and magnetic interface (16). Bidirectional wireless interface configured for bidirectional wireless data transmission via alternating electric field between medical device and an external device and may assume at least one OFF and one ON state, whereby wireless data transmission is possible only in ON state and function interface requires little or no energy in OFF state. Magnetic interface configured to constantly receive control signals transmitted via an alternating magnetic field from the external device. Magnetic interface configured to receive/process a data transmission start signal, such that magnetic interface or control unit generates a wireless interface activation. The bidirectional wireless interface is at least indirectly connected to the magnetic interface and is configured to switch from OFF to ON state in response to the wireless interface activation signal.

12 Claims, 4 Drawing Sheets

IMPLANTABLE MEDICAL DEVICE

This application takes priority from German Patent Application DE 10 2008 002 369.8, filed 11 Jun. 2008, the specification of which is hereby incorporated herein by reference.

BACKGROUND OF THE INVENTION

1. Field of the Invention

The invention relates to an implantable medical device such as an implantable cardiac pacemaker or an implantable cardioverter defibrillator (ICD). However, the invention is not limited to these specific implantable medical devices but instead fundamentally includes all electronically controlled implantable medical devices.

2. Description of the Related Art

Such implantable medical devices, e.g., cardiac pacemakers or ICDs, are often equipped with a bidirectional wireless interface today, making it possible to program these medical devices by means of an external device or to make data inquiries of the medical devices, e.g., physiological data acquired by the medical device. Based on the fact that implantable medical devices should have the smallest possible volume and therefore necessarily have only a limited amount of energy, which is usually available through a battery, for their operation, it is customary for the respective bidirectional wireless interface not to remain permanently in operation but instead to be activated preferably only when actually needed. The total energy consumption of the bidirectional wireless interface can be kept within limits over a longer period of time in this way. The bidirectional wireless interface can thus change back and forth between an OFF state and an ON state, such that the bidirectional wireless interface consumes little or no energy in the OFF state and is capable of wireless reception and transmission of data only in the ON state.

For this reason, such medical devices require an activation mechanism for programming over a bidirectional wireless interface to activate the bidirectional wireless interface of the medical device. For activation of the bidirectional wireless interface, i.e., to cause the bidirectional wireless interface to switch from an OFF state to an ON state, it is customary today to provide activators in the form of separate external devices or a programming head for inductive telemetry of a conventional programming device. It can also be anticipated that additional low-current receivers will be provided in a frequency range other than that of the bidirectional wireless interface for activation of the bidirectional wireless interface in the future.

Disadvantages of the aforementioned approaches include the fact that it is an additional external device, which is associated with costs, problems in introducing the external device into the sterile area in an operating room or the risk of loss of the external device or the disadvantages of an additional receiver in the implantable medical device. The latter causes costs, consumes power and must be approved. Furthermore, antenna tuning is critical when using a second high frequency because a compromise must be made here between the frequencies of the additional receiver for activation of the bidirectional wireless interface and the frequencies for the bidirectional wireless interface or a second antenna must be integrated into the electronic implant.

BRIEF SUMMARY OF THE INVENTION

Against the background of this prior art, the object of the present invention is to create an implantable medical device with a wireless interface having the simplest possible and inexpensive mechanism for remote activation of the wireless interface.

According to the invention, this object is achieved by an implantable medical device, in particular by an implantable cardiac pacemaker or an implantable cardioverter defibrillator (ICD) having a control unit connected to a bidirectional wireless interface for wireless data transmission by means of an alternating electric field and a magnetic interface for receiving data via an alternating magnetic field. The bidirectional wireless interface may assume at least one OFF state and one ON state, such that a wireless data transmission is possible only in the ON state and the wireless interface in the OFF state requires little or no energy. The magnetic interface is designed to be able to constantly receive control signals on the part of an external device to be transmitted by means of an alternating magnetic field. According to the invention, the magnetic interface is further designed to receive a data transmission start signal transmitted via an alternative magnetic field and to process it, e.g., to decode it in such a way that the magnetic interface or the control unit generates a wireless interface activation signal in response to reception of such a data transmission start signal. The bidirectional wireless interface is in turn connected at least indirectly to the magnetic interface according to the invention—e.g., via the control unit—and is designed to switch from the OFF state to the ON state in response to a wireless interface activation signal.

The invention is based on the finding that a magnetic interface for inductive telemetry is also present in typical implantable medical devices and can be utilized for activation of the bidirectional interface. In conventional electronic implants at the present time, a send-and-receive antenna for inductive telemetry is currently provided in the interior of a hermetically sealed metal housing, which can be penetrated only by an alternating magnetic field but not by an alternating electric field. Therefore, known communication methods are described as inductive methods in this context. Such known communication methods include communication between a programming device and an implant by means of an alternating magnetic field. In contrast with the activation mechanisms known at the present time by means of inductive telemetry (programming head or external activator), inductive telemetry is used only unidirectionally, not bidirectionally according to the present invention. In other words, the command (data transmission signal) for activation of the wireless interface is transmitted to the electronic implant by means of inductive telemetry (alternating magnetic field), but the response is via high-frequency wireless telemetry. The advantage is that the transmitting power of the external device for the transmission of the data transmission signal to the implant can be increased to an almost unlimited extent and the possible geometry of the transmission coil can be largely optimized. Optimization of the inductive transmission coil and energy in the electronic implant is greatly limited, however, due to the small geometry and the limited power supply.

The data transmission start signal is coded by a specific sequence in the alternating magnetic field, so that it can be identified unambiguously and decoded as the data transmission start signal by the magnetic interface (hereinafter also referred to as the inductive telemetry unit).

Another aspect of the present invention consists of an external device that is complementary to the implantable medical device. This external device also has a bidirectional wireless interface for the transmission of data by means of a high-frequency alternating electromagnetic field as well as an inductive transmission unit for transmitting a data transmission start signal by means of an alternating magnetic field.

An overall inventive system comprises an inventive implantable medical device and an inventive external device. To trigger a bidirectional data transmission between the external device and the implantable medical device, the external device first sends a data transmission start signal over the inductive transmission unit. If this data transmission start signal is received by an implantable medical device over its magnetic interface, the data transmission start signal is decoded by the magnetic interface or the control unit of the implantable medical device and a wireless interface activation signal is generated, causing the wireless interface of the implantable medical device to be activated.

The implantable medical device here is preferably designed so that immediately after activation of the wireless interface, the implantable medical device emits over said interface a wireless transmission start signal, which can be received by the external device and then initiates bidirectional data communication.

Alternatively, the implantable medical device may also be designed so that after activation of the wireless interface due to reception of a data transmission start signal and the wireless interface activation signal generated subsequently thereto, it waits for reception of a data packet over the wireless interface before the implantable medical device itself transmits a data packet over the wireless interface. In this context, the external device is designed to send an initial data packet over the wireless interface of the external device after transmitting a data transmission start signal over the inductive transmission unit. When the data transmission start signal transmitted by the external data device reaches the implantable medical device and triggers the activation of its wireless interface, and then when the initial data packet transmitted by the external device reaches the wireless interface of the implantable medical device, bidirectional data transmission between the external device and the implantable medical device is initiated.

According to a preferred variant of the embodiment, the data transmission start signal is specific for a respective implantable medical device. With respect to a preferred inventive implantable medical device, this means that its magnetic interface or its control unit is designed to generate a wireless interface activation signal after receipt of a data transmission start signal only when the data transmission start signal received over the magnetic interface contains a device-specific identifier for the specific implantable medical device.

The implantable medical device and/or its control unit or its magnetic interface is designed to respond only to data transmission start signals having a specific identifier.

According to another preferred variant of the embodiment of the invention, the external device is designed to generate a data transmission start signal containing a wireless channel identifier which identifies a transmission channel (frequency range) to be used for bidirectional data transmission over the wireless interface. In this context, the implantable medical device is preferably designed to receive and process a corresponding data transmission start signal over the magnetic interface, such that the wireless channel identifier is decoded and then the wireless interface is set up for data transmission in this transmission channel.

In conjunction with the preferred embodiment variant mentioned last, the external device is preferably designed to first check (scan) the available data transmission channels to detect a preferably free and undisturbed transmission channel before generating a data transmission start signal containing a wireless channel identifier of a transmission channel to be used. In this context, the external device is also designed to add the wireless channel identifier of the transmission channel that is free and has the least interference to the data transmission start signal to be transmitted.

Especially preferred are a system and system components (implantable medical device and external device) in which the data transmission start signal contains a device-specific identifier for the particular implantable medical device and a wireless channel identifier in the sense described above.

In addition, the implantable medical device may be designed, so that the wireless interface can be activated and/or deactivated by means of a wireless interface activation signal generated at the magnetic interface. This activation and/or deactivation may be accomplished through corresponding control commands that are to be received over the magnetic interface or the wireless interface or both.

In this way, the activation of the wireless interface can be deactivated via a corresponding data transmission start signal in a targeted manner. This is helpful in particular when the data transmission start signal is not device-specific, i.e., does not contain a device-specific identifier for a respective implantable medical device. It is thus possible with such implantable medical devices to deactivate the activation of the wireless interface via a data transmission start signal and a corresponding wireless interface activation signal in which no bidirectional data transmission is pending in the foreseeable period of time. Accordingly, the possibility of activation of the wireless interface via data transmission start signals transmitted by alternating magnetic field is activated only with the implantable medical devices in which bidirectional data transmission via the wireless interface is desired in the short range. It is thus possible to prevent the number of activated implantable medical devices from exceeding the number of available wireless transmission channels.

In conjunction with a data transmission start signal that can be received by several implantable medical devices simultaneously, it is advantageous if the external device assigns response times to the data transmission start signal for implantable medical devices identified by a corresponding device identifier. The implantable medical devices in this situation are designed so that they allow data transmission over the wireless interface only at the assigned response times. This makes it possible to avoid collisions in data transmission over the bidirectional wireless interfaces.

The object defined in the introduction is also achieved according to this invention by a method for initiating a bidirectional data transmission between an implantable medical device having a magnetic interface and a function interface and an external device having an inductive transmission unit and a function interface in which first a data transmission start signal is transmitted from the inductive transmission unit to the magnetic interface and then the function interface of the implantable medical device is switched to its activated state.

Other advantageous process variants are derived from the preferred device variants as well as the following description of exemplary embodiments.

BRIEF DESCRIPTION OF THE DRAWINGS

The invention will now be explained in greater detail on the basis of exemplary embodiments with reference to the figures, in which.

DETAILED DESCRIPTION OF THE INVENTION

Figure 1:
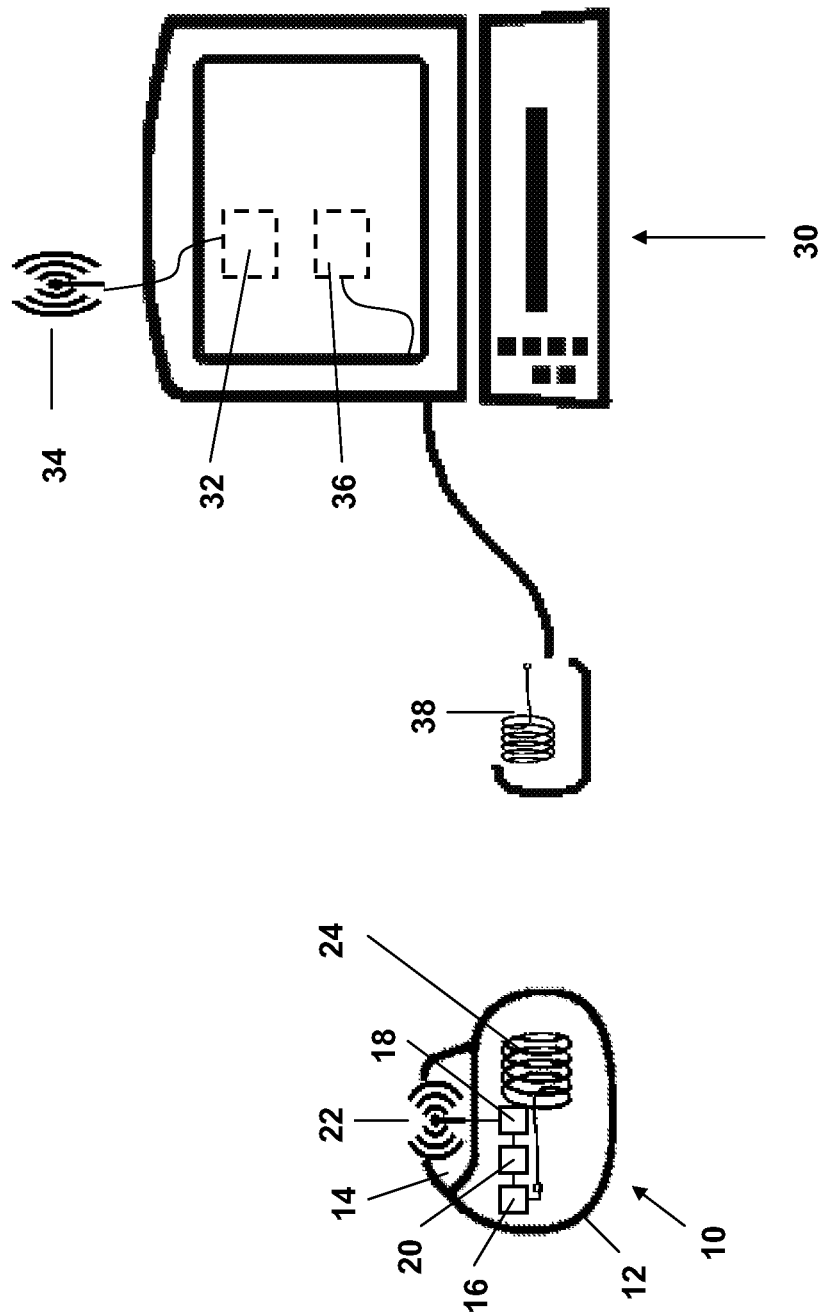
FIG. 1 shows an implantable medical device and an external device according to a first embodiment variant of the invention.

FIG. 1 shows an implantable medical device 10 in combination with an external device 30, together forming a system for bidirectional data transmission between the implantable medical device and the external device.

The implantable medical device 10 is presented in the exemplary embodiment as an implantable cardiac pacemaker having a housing 12 and a header 14. In addition to the usual components of such an implantable medical device, the implantable medical device 10 has a magnetic interface 16 and a wireless interface 18, both of which are connected to a control unit 20 of the implantable medical device 10. The function interface 18 is connected to an antenna 22 accommodated in the header 14, which is made of plastic and therefore provides shielding from alternating electric fields, outside of the metallic housing 12 of the implantable medical device 10.

A receiver coil 24 of a magnetic interface 16 is accommodated in the metallic housing 12 of the implantable medical device 10. Over the receiver coil 24, the magnetic interface can receive control sequences transmitted by means of an alternating magnetic field. The alternating magnetic field is capable of penetrating the metallic housing 12 of the implantable medical device.

The external device 30 also has a function interface 32 with an antenna 34 as well as an inductive transmission unit 36 with an induction coil 38.

The inductive transmission unit 36 is designed to transmit control sequences over the induction coil 38 by means of an alternating magnetic field.

The wireless interface 32 of the external device 30 is designed to allow bidirectional communication with the wireless interface 18 of the implantable medical device.

As indicated in FIG. 1, at least the induction coil 38 of the inductive transmission unit 36 is accommodated in a comparatively mobile component of the external device 30, connected by wire to the remainder of the external device 30, which serves as a programming head. On the whole, the external device 30 serves as the programming device for the implantable medical device 10. By accommodating the induction coil 38 of the inductive transmission unit 36 in the movable programming head 40 of the external programming device 30, the induction coil 38 can easily be accommodated in the vicinity of the implantable medical device even if implanted in a patient's body.

Figure 2:
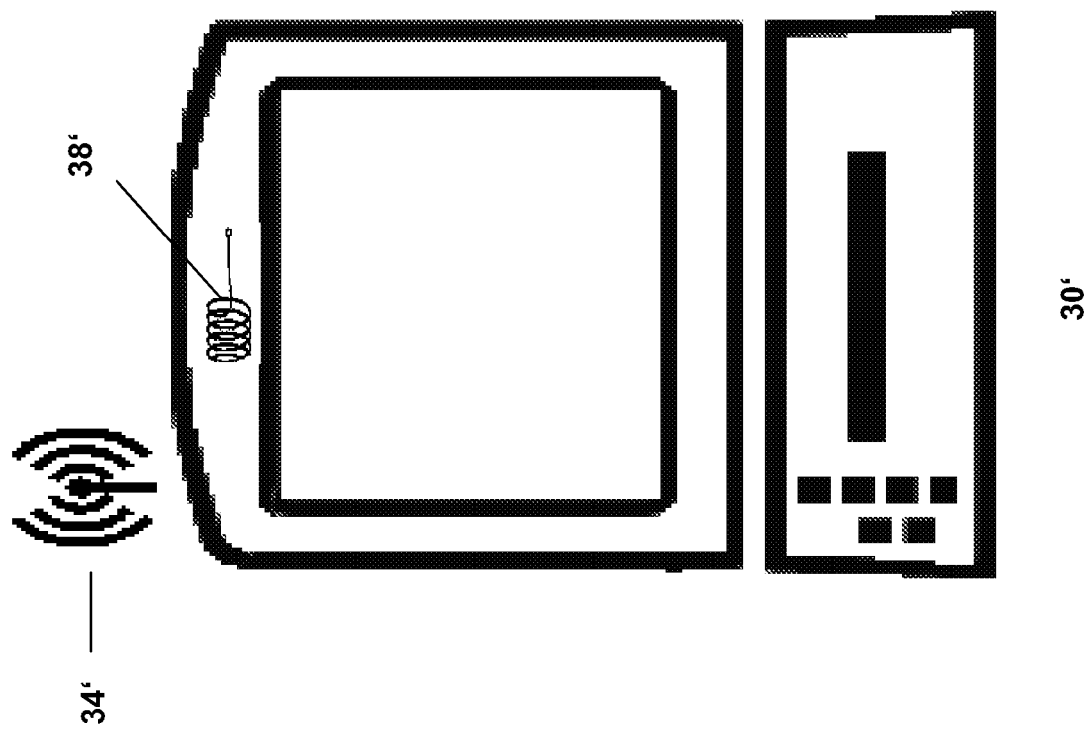
FIG. 2 shows an alternative external device.

Alternatively, the induction coil 38' of the inductive transmission unit 36 may also be accommodated in the housing of the external device 30' as illustrated in FIG. 2. The external device 30 may be designed so that it can be held in the hand in the manner of a cellular telephone.

The wireless interfaces 18 and 32 of the implantable medical device 10 and/or of the external device 30 are designed to wirelessly transmit data, e.g., physiological data compiled by the implantable medical device 10 and to do so by wireless transmission by means of an alternating electric field, preferably in the MICS frequency band reserved specifically for these purposes.

Furthermore, a wireless exchange of control sequences between the external device 30 and the implantable medical device 10 is possible by way of the inductive transmission unit 36 and the magnetic interface 18. As shown in FIGS. 1 and 2, the external device 30 may therefore have one or more induction coils at different locations.

The wireless interface 18 of the implantable medical device 10 is designed so that it may assume both an activated state and a deactivated state of the type described above. To protect a battery (not shown in FIG. 1) of the implantable medical device 10 as much as possible, it is desirable if the wireless interface 18 of the implantable device 10 is activated only when it is in fact needed for wireless data transmission between the implantable medical device 10 and the external device 30. The wireless interface 18 of the implantable medical device 10 is therefore designed so that it turns off automatically after a data transmission is successfully concluded, i.e., it is switched to its OFF state.

To also activate the wireless interface 18 of the implantable medical device 10 from outside of the implantable medical device 10, i.e., to be able to switch it to the activated state, the wireless interface 18 is connected at least indirectly to a magnetic interface 16 (via the control unit 20 in the exemplary embodiment). The magnetic interface 16 is designed to receive control sequences representing a data transmission start signal via its receiver coil 24. The control sequences are represented by an alternating magnetic field, which is demodulated by the magnetic interface 16. Then the control sequences can be decoded by the magnetic interface 16 or the control unit 20. If the received control sequences represent a data transmission start signal, the control unit 20 generates a wireless interface activation signal, which causes the wireless interface 18 of the implantable medical device 10 to be activated or turned on, i.e., switched to its activated state.

As already described above, the implantable medical device 10 may also be designed so that not just any data transmission start signal leads immediately to generation of a wireless interface activation signal. Instead, the respective data transmission start signal may also contain a device-specific identifier, as a result of which only an implantable medical device identified with this device identifier generates a wireless interface activation signal after receiving the data transmission start signal. The data transmission start signal may also contain a wireless channel identifier, which characterizes a certain transmission channel in the MICS frequency band. The implantable medical device 10 then adjusts the wireless interface 18 so that it transmits data in this transmission channel.

The implantable medical device 10 may also comprise a timer (not shown in FIG. 1) and may be designed to derive a response time identifier from a control sequence containing a data transmission start signal, identifying a point in time at which the implantable medical device, in particular its control unit 20, generates a wireless interface activation signal and thus activates the wireless interface 18.

Additional details of the sequence of initiation of a bidirectional wireless data transmission over the wireless interfaces 18 and 32 of the implantable medical device 10 and/or the external device 30 are derived from the following description of alternative sequences.

Figure 3:
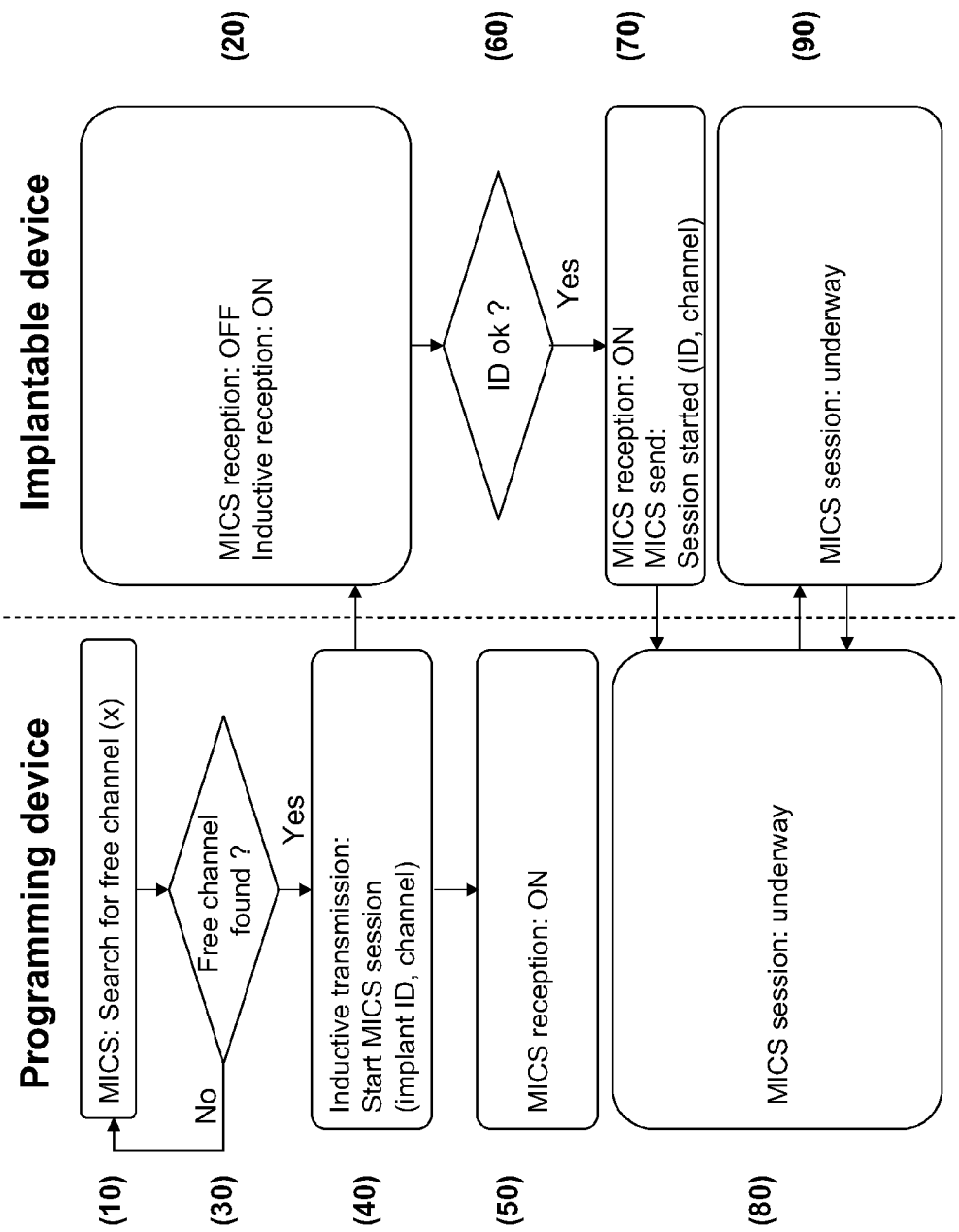
FIG. 3 shows a first variant of the flow chart for activation of a bidirectional data communication.

The basic sequence of activation of the MICS telemetry of an implantable medical device by the unidirectional inductive telemetry (i.e., data transmission via an alternating magnetic field) is depicted in FIG. 3, which follows.

First, the channel having the least interference in the MICS band is selected by the programming device as the external device (10).

Meanwhile, the MICS telemetry, i.e., the wireless interface, in the implanted medical device is deactivated. Reception for the inductive telemetry, i.e., the magnetic interface of the implantable medical device, is activated (20).

When the free channel having the least interference has been identified by the programming device (30), the programming device sends a data transmission start signal to the implantable medical device over the inductive transmission unit for activation of the MICS wireless interface. This data transmission start signal contains information about the implant ID to be activated in the form of a device identifier and contains the MICS channel information for establishing the connection (40) in the form of a wireless channel identifier.

The programming device then starts its own MICS wireless interface after transmission of the data transmission start signal and waits for confirmation of the activation of the implantable medical device (50).

The implantable medical device receives this data transmission start signal via the inductive receiver of its magnetic interface and compares the device identifier thereby sent (implant ID) with its own implant ID. If they match (60), then the MICS wireless interface in the implantable medical device is activated and a confirmation of the activation and of the implant ID in the form of a wireless transmission start signal is sent to the programming device via the MICS channel thereby identified (70).

Next the bidirectional data transmission on the MICS band between the programming device (80) and the implantable medical device (90) is continued.

Figure 4:
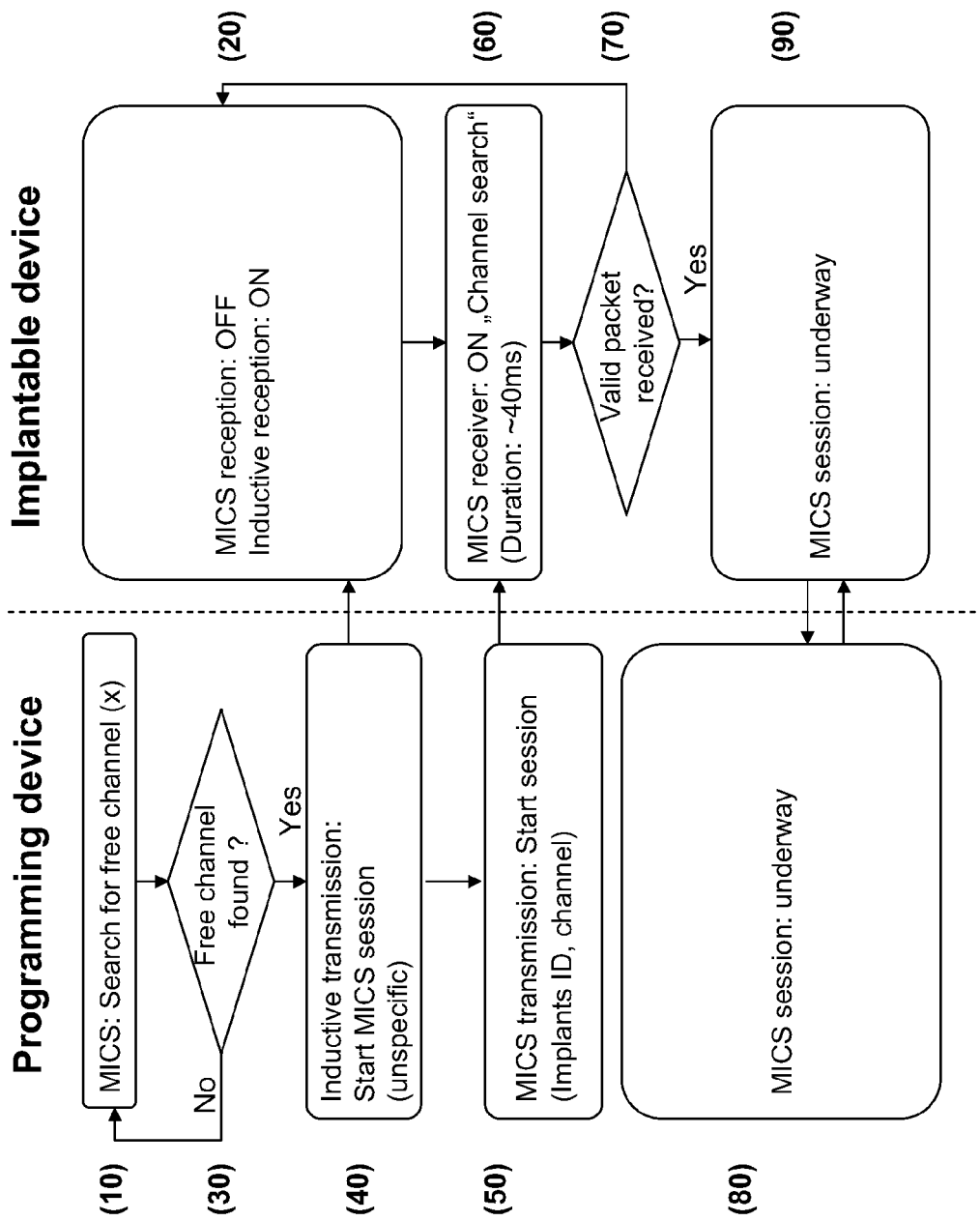
FIG. 4 shows a flow chart of an alternative indexing of a bidirectional data communication between an implantable medical device and an external device.

FIG. 4 shows an alternative implementation, where it is assumed that only very nonspecific information can be transmitted over a large range via inductive telemetry.

The programming device as an external device first searches for the free channel in the MICS band (10) which has the least interference. Meanwhile the receiver of the magnetic interface for inductive telemetry has been activated in the implantable medical device but the (current-intensive) MICS reception via the wireless interface has been shut down (20).

When a free channel is found by the programming device (30), it sends a nonspecific command as a data transmission start signal via the inductive method (40). When received by the implantable medical device, this command leads to brief activation of the MICS receiver of the wireless interface, which then executes a channel search in a defined time slot after activation (60). If the wireless interface of the implantable medical device receives a valid data packet on one of the MICS channels, then the implantable medical device and the programming device initiate a communication session on the MICS protocol (80, 90). If the wireless interface of the implantable medical device does not receive a valid packet, the implantable medical device automatically deactivates its wireless interface and returns to the starting state (20).

The inventive approach offers the advantage that "remote activation" of the wireless interface of an implantable medical device is possible without the additional expense of a separate RF activator or an additional RF receiver. Furthermore, the initial application of the programming head in the near range of the implantable medical device, which is possible as an alternative is not necessary so that RF activation in the operating room is possible without having to introduce the programming head into the sterile area. Likewise, a search function of all implantable medical devices within range can be implemented (outpatient clinic, waiting room, first aid station).

What is claimed is:

1. An implantable medical device (10), comprising:
   a bidirectional wireless interface (18);
   a magnetic interface (16) configured to activate said bidirectional wireless interface via a unidirectional inductive activation mechanism;
   a control unit (20) connected to the bidirectional wireless interface (18) wherein the control unit (20) is further connected to the magnetic interface (16);
   wherein the bidirectional wireless interface (18) is configured to transmit data bidirectionally and wirelessly via an alternating electric field between the implantable medical device and an external device;
   wherein the bidirectional wireless interface (18) may assume at least one OFF state and one ON state, such that wireless data transmission is possible only in the one ON state and wherein the bidirectional wireless interface (18) in the at least one OFF state requires less energy than the one ON state or no energy;
   wherein the magnetic interface (16) is configured to unidirectionally communicate with said external device to receive control signals transmitted via an alternating magnetic field from the external device without transmission of information over said magnetic interface to said external device to implement said unidirectional inductive activation mechanism;
   wherein the magnetic interface (16) is further configured to receive a data transmission start signal and to process the data transmission start signal, such that the magnetic interface (16) or the control unit (20) generates a wireless interface activation signal in response to reception of the data transmission start signal;
   wherein the bidirectional wireless interface (18) is connected at least indirectly to the magnetic interface (16);
   wherein the bidirectional wireless interface (18) is configured to switch from the at least one OFF state to the one ON state in response to the wireless interface activation signal;
   wherein the magnetic interface (16) or the control unit (20) is configured to generate the wireless interface activation signal after the data transmission start signal is received only if the data transmission start signal received via the magnetic interface contains a device-specific identifier for a specific implantable medical device;
   wherein the external device is configured to assign a response time to the data transmission start signal; and,
   wherein the implantable medical device is configured to
      extract a response time identifier from the data transmission start signal identifying the response time, wherein the response time is a point in time at which the implantable device generates the wireless interface activation signal;
      extract the device-specific identifier; and,
      generate the wireless interface activation signal only when the response time defined by the response time identifier has been reached.

2. The implantable medical device according to claim 1, wherein the implantable medical device is configured to transmit a wireless transmission start signal via the bidirectional wireless interface immediately after activation of the bidirectional wireless interface, such that said wireless transmission start signal can be received by the external device and initiates a bidirectional data communication.

3. The implantable medical device according to claim 1, wherein the implantable medical device is configured so that after activation of the bidirectional wireless interface due to reception of the data transmission start signal and of the wireless interface activation signal generated thereupon, the implantable medical device waits for reception of a data packet over the bidirectional wireless interface before the implantable medical device sends the data packet over the bidirectional wireless interface.

4. The implantable medical device according to claim 1, wherein the implantable medical device is configured so that the bidirectional wireless interface is activated and/or deactivated with a control command received by the magnetic interface.

5. The implantable medical device according to claim 1, wherein the data transmission signal received via said magnetic interface comprises a wireless channel identifier and wherein the wireless channel identifier is decoded and then the bidirectional wireless interface is configured to transmit data over a channel identified by the wireless channel identifier.

6. An external device comprising:
   a second bidirectional wireless interface configured to transmit data via an alternating electromagnetic field between the external device and an implantable medical device; and,
   an inductive transmission unit configured to transmit a data transmission start signal to the implantable medical device via an alternating magnetic field to unidirectionally communicate with said implantable medical device without receipt of information over said inductive transmission unit to implement a unidirectional inductive activation mechanism;
wherein the implantable medical device comprises
   a bidirectional wireless interface;
   a magnetic interface configured to activate said bidirectional wireless interface via a unidirectional inductive activation mechanism; and
   a control unit connected to the bidirectional wireless interface;
      wherein the control unit is further connected to the magnetic interface,
      wherein the magnetic interface or the control unit is configured to generate the wireless interface activation signal after the data transmission start signal is received only if the data transmission start signal received via the magnetic interface contains a device-specific identifier for a specific implantable medical device, and,
      wherein the magnetic interface is further configured to receive a data transmission start signal and to process the data transmission start signal such, that the magnetic interface or the control unit generates a wireless interface activation signal in response to reception of the data transmission start signal;
wherein the external device is configured to assign a response time to the data transmission start signal; and,
wherein the implantable medical device is configured to
   extract a response time identifier from the data transmission start signal identifying the response time, wherein the response time is a point in time at which the implantable device generates the wireless interface activation signal;
   extract the device-specific identifier; and,
   generate the wireless interface activation signal only when the response time defined by the response time identifier has been reached.

7. The external device according to claim 6, wherein the external device is configured to generate the data transmission start signal for transmission over the inductive transmission unit.

8. The external device according to claim 6, wherein the data transmission start signal contains a wireless channel identifier, and wherein the external device is configured to:
   first check available transmission channels before the external device generates the data transmission start signal that contains the wireless channel identifier of the transmission channel or frequency to be used, in order to ascertain a free transmission channel with as little interference as possible.

9. The external device according to claim 6, wherein the external device is configured to generate the data transmission start signal that contains a wireless channel identifier that identifies a transmission channel or frequency range to be used for bidirectional data transmission over the second bidirectional wireless interface.

10. A system for bidirectional data transmission between an implantable medical device according to claim 1 and an external device comprising:
   a second bidirectional wireless interface configured to transmit data via an alternating electromagnetic field between the external device and the implantable medical device; and,
   an inductive transmission unit configured to transmit the data transmission start signal to the implantable medical device via an alternating magnetic field.

11. A method for initiating a bidirectional data transmission between an implantable medical device having a magnetic interface and a first wireless interface and an external device having an inductive transmission unit and a second wireless interface, comprising
   transmitting a data transmission start signal from the inductive transmission unit to the magnetic interface wherein said data transmission signal comprises a wireless channel identifier that controls a channel utilized by said first wireless interface; and,
   switching the first wireless interface in the implantable medical device to an activated state;
      wherein the external device is configured to assign a response time to the data transmission start signal; and,
      wherein the implantable medical device is configured to
         extract a response time identifier from the data transmission start signal identifying the response time, wherein the response time is a point in time at which the implantable device generates the wireless interface activation signal;
         extract the device-specific identifier; and,
         generate the wireless interface activation signal only when the response time defined by the response time identifier has been reached.

12. The method according to claim 11, further comprising:
   searching for a free transmission channel via the external device before transmitting the data transmission start signal.

* * * * *